United States Patent
Honda et al.

(10) Patent No.: US 9,221,030 B2
(45) Date of Patent: Dec. 29, 2015

(54) METHOD FOR PRODUCING WATER-ABSORBENT RESIN

(75) Inventors: Noriko Honda, Kakogawa (JP); Ayaka Watanabe, Saitama (JP); Kimihiko Kondo, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 36 days.

(21) Appl. No.: 14/000,150

(22) PCT Filed: Mar. 12, 2012

(86) PCT No.: PCT/JP2012/056300
§ 371 (c)(1),
(2), (4) Date: Aug. 16, 2013

(87) PCT Pub. No.: WO2012/132861
PCT Pub. Date: Oct. 4, 2012

(65) Prior Publication Data
US 2013/0324396 A1 Dec. 5, 2013

(30) Foreign Application Priority Data

Mar. 28, 2011 (JP) ................ 2011-070727

(51) Int. Cl.
*B01J 20/26* (2006.01)
*C08F 6/00* (2006.01)
*C08F 20/06* (2006.01)
*C08F 4/04* (2006.01)
*C08F 2/20* (2006.01)
*A61L 15/60* (2006.01)

(52) U.S. Cl.
CPC ............ *B01J 20/261* (2013.01); *A61L 15/60* (2013.01); *C08F 2/20* (2013.01); *C08F 4/04* (2013.01); *C08F 6/006* (2013.01); *C08F 6/008* (2013.01); *C08F 20/06* (2013.01)

(58) Field of Classification Search
CPC .......... B01J 20/26; B01J 20/30; B01J 20/261; C08F 20/06; C08F 4/28; C08F 2/18; C08F 251/00; C08F 2/44
USPC ...................... 502/402; 526/317.1
See application file for complete search history.

(56) References Cited

U.S. PATENT DOCUMENTS

| 8,859,700 | B2 * | 10/2014 | Yokoyama et al. ........ 526/317.1 |
| 2005/0085604 | A1 | 4/2005 | Handa et al. |
| 2009/0182092 | A1 | 7/2009 | Yokoyama et al. |
| 2010/0197491 | A1 | 8/2010 | Takatori et al. |
| 2010/0256308 | A1 | 10/2010 | Takatori et al. |

FOREIGN PATENT DOCUMENTS

| CN | 101479297 A | 7/2009 | |
| CN | 101765637 A | 6/2010 | |
| CN | 101835814 A | 9/2010 | |
| EP | 1 882 701 A1 | 1/2008 | |
| EP | 2 599 795 A1 | 6/2013 | |
| EP | 2 599 795 A1 * | 6/2013 | ............ C08F 2/18 |
| JP | 64-062317 * | 3/1989 | ........... C08F 251/00 |
| JP | 64-62317 A | 3/1989 | |
| JP | 2001-2726 A | 1/2001 | |
| JP | 2001-11106 A | 1/2001 | |
| JP | 2002-105125 * | 4/2002 | ............ A01G 1/00 |
| JP | 2002-105125 A | 4/2002 | |
| JP | 2002-241428 A | 8/2002 | |
| JP | 2003-206305 A | 7/2003 | |
| JP | 2006-176570 A | 7/2006 | |
| JP | 2008-7567 A | 1/2008 | |
| JP | 2008-133396 * | 6/2008 | ............ A61F 13/49 |
| JP | 2008-133396 A | 6/2008 | |
| WO | WO 03/059962 A1 | 7/2003 | |

OTHER PUBLICATIONS

English translation of International Preliminary Report on Patentability and Written Opinion mailed Oct. 10, 2013.
International Search Report issued in Apr. 17, 2013, in PCT International Application No. PCT/JP2012/056300.
Chinese Search Report dated Dec. 2, 2014 issued in Chinese Patent Application No. 201280015717.2.
Search Report issued in SG Application No. 2013064993 dated Nov. 13, 2014.
Supplementary European Search Report dated Oct. 1, 2014, issued in European Patent Application No. 12765406.9.
Written Opinion issued in SG 2013064993 dated Nov. 13, 2014.

* cited by examiner

*Primary Examiner* — Robert Harlan
(74) *Attorney, Agent, or Firm* — Birch, Stewart, Kolasch & Birch, LLP

(57) ABSTRACT

A method for producing a water-absorbent resin includes a polymerization step of polymerizing a polymerizable component containing a water-soluble ethylenically unsaturated monomer dissolved in water using a water-soluble azo-type radical polymerization initiator to obtain a reaction system including a water-absorbent resin precursor, and a dehydration step of removing water from the reaction system by heating. In the dehydration step, a water-soluble radical polymerization initiator is added to the reaction system at any first dehydration stage when the residual water rate calculated by the formula (1) is 50% or more, and a reducing substance is added to the reaction system at any second dehydration stage when the residual water rate decreases from that at the first dehydration stage by 10% or more. According to this production method, a water-absorbent resin having satisfactory water-absorption capacity can be produced while suppressing the content of residual monomers.

$$\text{Residual Water Rate (\%)} = \frac{\text{Mass of Water Remaining in Reaction System}}{\text{Mass of Water-Soluble Ethylenically Unsaturated Monomer Used in Polymerization Step}} \times 100 \quad (1)$$

13 Claims, 1 Drawing Sheet

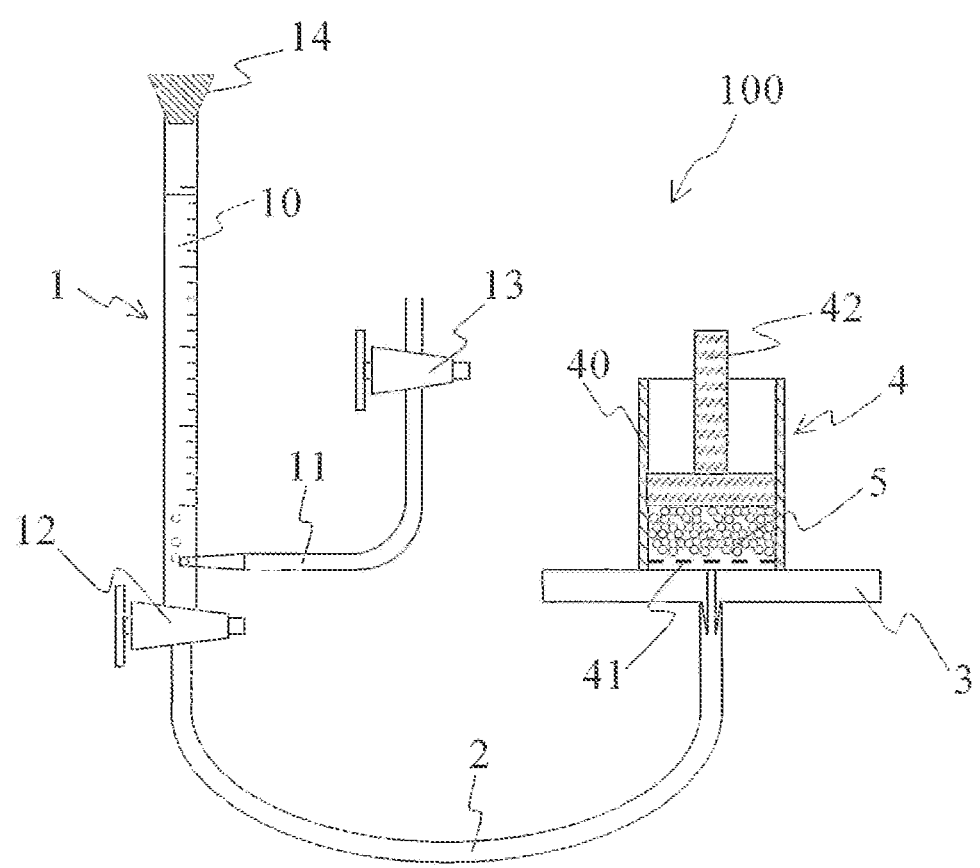

US 9,221,030 B2

METHOD FOR PRODUCING WATER-ABSORBENT RESIN

TECHNICAL FIELD

The present invention relates to a method for producing a water-absorbent resin, in particular, to a method for producing a water-absorbent resin by polymerizing polymerizable component containing a water-soluble ethylenically unsaturated monomer dissolved in water using a water-soluble azo-type radical polymerization initiator.

BACKGROUND ART

A water-absorbent resin is widely used in hygienic materials such as disposable diapers and sanitary napkins, commodities such as pet sheets, and industrial materials such as water blocking materials for cable. While many types of water-absorbent resins are known in accordance with various applications, a water-absorbent resin made of a polymer of water-soluble ethylenically unsaturated monomer is mainly used in hygienic materials such as disposable diapers and sanitary napkins. For the water-absorbent resin made of a polymer of water-soluble ethylenically unsaturated monomer used in a hygienic material, high safety is generally required due to a possibility of direct contact to the human body, and absorption capacity that can rapidly and stably absorb and retain a large amount of body fluids when contacting to body fluids such as urine and blood is also required. Particularly, recent hygienic materials tend to be made thinner for comfortableness in wearing and portability, and thus are urged to use a smaller amount of the water-absorbent resin and, at the same time, to increase absorption capacity. Therefore, higher water-absorption capacity of a water-absorbent resin itself is now required.

A water-absorbent resin made of a polymer water-soluble ethylenically unsaturated monomer can achieve higher water absorption generally by lowering the degree of crosslinking. However, this type of water-absorbent resin is often produced by polymerizing a water-soluble ethylenically unsaturated monomer using a persulfate as a polymerization initiator. In this case, self-crosslinking is likely to progress in the produced water-absorbent resin, thus it is difficult to obtain a water-absorbent resin with high water-absorption capacity. For the improvement in this respect, Patent Literature 1 describes that an azo-type compound capable of suppressing self-crosslinking is used as a polymerization initiator in place of a persulfate. However, since the polymerization rate of a water-soluble ethylenically unsaturated monomer is less likely to rise in the case of using an azo-type compound as a polymerization initiator, a lot of unreacted monomers remain in the produced water-absorbent resin. Furthermore, the amount of unreacted monomers in the water-absorbent resin tends to increase by partial decomposition of the water-absorbent resin in the dehydration step of removing water by heating from a reaction system containing the produced water-absorbent resin. When the water-absorbent resin containing unreacted monomers and monomers produced by decomposition of part of the ter-absorbent resin (hereinafter, these monomers ray be collectively-referred to as "residual monomers") is used in a hygienic material, it may cause skin problems such, as rush and inflammation on a user.

Therefore, a method for suppressing the content of residual monomers in a water-absorbent resin is suggested. For example, Patent Literature 2 describes a method of adding a radical polymerization initiator before drying or during drying a slurry containing a water-absorbent resin obtained by polymerizing a water-soluble ethylenically unsaturated monomer by a reversed-phase suspension polymerization method. Also, Patent Literature 3 describes a method of adding a reducing substance such as a sulfite and a method of adding a prescribed azo compound together with a reducing substance, after the polymerization of a water-soluble ethylenically unsaturated monomer.

However, the water-absorbent resin produced in accordance with these methods has a defect in water-absorption capacity, which is an essential quality required for a water-absorbent resin, while the content of residual monomers is suppressed.

PRIOR ART LITERATURES

Patent Literatures

Patent Literature 1: Japanese Patent Application Laid-Open No. 2006-176570
Patent Literature 2: Japanese Patent Application Laid-Open No. 2002-105125
Patent Literature 3: Japanese Patent Application Laid-Open No. 64-62317

SUMMARY OF THE INVENTION

Problems to be Solved by the Invention

An object of the present invention is to produce a water-absorbent resin that shows satisfactory water-absorption capacity while suppressing the content of residual monomers.

Means for Solving the Problems

A method for producing a water-absorbent resin according to the present invention includes a polymerization step of polymerizing a polymerizable component containing water-soluble ethylenically unsaturated monomer dissolved in water using a water-soluble azo-type radical polymerization initiator to obtain a reaction system containing water-absorbent resin precursor, and a dehydration step of removing water from the reaction system by heating. In the dehydration step, a water-soluble radical polymerization initiator is added to the reaction system at any first dehydration stage when the residual water rate calculated by the following formula (1) is 50% or more, and a reducing substance is added to the reaction system at any second dehydration stage when the residual water rate decreases from that at the first dehydration stage by 10% or more.

[Formula 1]

$$\text{Residual Water Rate (\%)} = \frac{\text{Mass of Water Remaining in Reaction System}}{\text{Mass of Water-Soluble Ethylenically Unsaturated Monomer Used in Polymerization Step}} \times 100 \quad (1)$$

In the polymerization step of this production method, it is usually preferred that the polymerizable component is polymerized by a reversed-phase suspension polymerization method. In this polymerization method, the polymerizable component may be further added to be polymerized, to a slurry obtained by progress of the polymerization of the polymerizable component. In this case, the addition of the polymerizable component to the slurry and the polymerization may be repeated.

The water-soluble azo-type radical polymerization initiator used in the polymerization step of this production method is usually at least one selected from the group consisting of 2,2'-azobis(2-amidinopropane)dihydrochloride, 2,2'-azobis[2-[1-(2-hydroxyethyl)-2-imidazolin-2-yl]propane]dihydrochloride, and 2,2'-azobis[N-(2-carboxyethyl)-2-methylpropionamidine]tetrahydrate.

The water-soluble radical polymerization initiator used in the dehydration step of this production method is usually at least one selected from the group consisting of potassium persulfate, sodium persulfate, and 2,2'-azobis[2-(N-phenylamidino)propane]dihydrochloride, and the reducing substance is usually at least one selected from the group consisting of sulfurous acid, a sulfite, hydrogen sulfite and a bisulfite.

In the production method of the present invention, the amount of the water-soluble radical polymerization initiator added to the reaction system is usually preferably set to 0.01 to 0.15 mol % of the total amount of the water-soluble ethylenically unsaturated monomer used in the polymerization step. In addition, the amount of the reducing substance added to the reaction system is usually preferably set to 0.0001 to 0.002 mol % of the total amount of the water-soluble ethylenically unsaturated monomer used in the polymerization step.

In an embodiment of the production method of the present invention, a water-absorbent resin precursor is subjected to a post-crosslinking treatment in the dehydration step.

In the method for producing a water-absorbent resin according to the present invention, since a water-soluble radical polymerization initiator and a reducing substance are separately added in a prescribed stage in this order in the dehydration step of the reaction system, a water-absorbent resin having satisfactory water-absorption capacity can be produced while suppressing the content of residual monomers.

The present invention according to another standpoint is directed to a water-absorbent resin, and this water-absorbent resin is obtainable by the production method of the present invention. The content of residual monomers in this water-absorbent resin is usually 100 ppm or less. One embodiment of this water-absorbent resin is in powdery form having a mass average particle size of 200 to 600 µm, and has a retention capacity of saline solution of 40 to 60 g/g and an absorption capacity of saline solution under a load of 4.14 kPa of 20 ml/g or more.

Since the water-absorbent resin of the present invention is produced by the production method of the present invention, the amount of residual monomers is small, and water-absorption capacity is excellent.

The present invention according to still another standpoint is directed to a hygienic material. This hygienic material includes a liquid permeable sheet, a liquid impermeable sheet, and an absorbent material retained between these sheets, and the absorbent material contains the water-absorbent resin of the present invention. The absorbent material is, for example, a composite of the water-absorbent resin of the present invention and a hydrophilic fiber.

The hygienic material of the present invention uses the water-absorbent resin produced by the production method of the present invention, thus is less likely to cause skin problems due to residual monomers and has excellent water-absorption capacity.

Other objects and effects of the present invention will be mentioned in the following detailed description.

BRIEF DESCRIPTION OF THE DRAWINGS

FIG. 1 A schematic view of an apparatus used in Examples for the measurement of a water-absorption capacity under load.

EMBODIMENTS OF THE INVENTION

In the method for producing a water-absorbent resin according to the present invention, first, a polymerizable component containing a water-soluble ethylenically unsaturated monomer is polymerized to prepare a water-absorbent resin (polymerization step). The water-absorbent resin prepared herein is to be chemically treated in the below-mentioned dehydration step, and thus termed as "water-absorbent resin precursor" for the sake of convenience.

A water-soluble ethylenically unsaturated monomer used herein is not particularly limited so long as it can be used in the production of a water-absorbent resin, and examples thereof include acrylic acid, methacrylic acid, 2-acrylamide-2-methylpropanesulfonic acid and alkali metal salts thereof, 2-methacrylamide-2-methylpropanesulfonic acid and alkali metal salts thereof, nonionic water-soluble ethylenically unsaturated monomers, and amino group-containing water-soluble ethylenically unsaturated monomers and quaternized products thereof, and the like. In the examples, a lithium salt, a sodium salt or a potassium salt is usually used as the alkali metal salt. In addition, examples of the nonionic water-soluble ethylenically unsaturated monomer include acrylamide, methacrylamide, N,N-dimethylacrylamide, 2-hydroxyethyl acrylate, 2-hydroxyethyl methacrylate, N-methylolacrylamide, N-methylolmethacrylamide, and the like. Furthermore, examples of the amino group-containing water-soluble ethylenically unsaturated monomer include diethylaminoethyl acrylate, diethylaminoethyl methacrylate, diethylaminopropyl acrylate, diethylaminopropyl methacrylate, and the like.

The water-soluble ethylenically unsaturated monomer can be used in combination of two or more kinds.

Examples of preferred water-soluble ethylenically unsaturated monomers include acrylic acid and alkali metal salts thereof, methacrylic acid and alkali metal salts thereof, acrylamide, methacrylamide, and N,N-dimethylacrylamide since they are easily available industrially. Examples of particularly preferred water-soluble ethylenically unsaturated monomers include acrylic acid, and alkali metal salts thereof and methacrylic acid and alkali metal salts thereof since they can economically produce a water-absorbent resin.

In the present invention, the water-soluble ethylenically unsaturated monomer is dissolved in water and used as an aqueous solution. The concentration of the water-soluble ethylenically unsaturated monomer in an aqueous solution is usually preferably set to 15% by mass or more and a saturated concentration or less.

When the water-soluble ethylenically unsaturated monomer contains an acid group, the aqueous solution of the water-soluble ethylenically unsaturated monomer may be one in which the acid group is neutralized by addition of an alkali metal compound. The alkali metal compound used for this purpose is not particularly limited, and is usually a hydroxide. As the alkali metal, lithium, sodium or potassium is usually used, sodium or potassium is preferably used, and sodium is particularly preferably used. The neutralization degree achieved by addition of the alkali metal compound is preferably set in the range of 10 to 100 mol % of the acid group of the water-soluble ethylenically unsaturated monomer before neutralization, from the viewpoint of increasing the er-absorption rate with enhancing the osmotic pressure of the obtained water-absorbent resin and not causing a problem in safety of the water-absorbent resin by the presence of an excess alkali metal compound.

The polymerizable component used in the polymerization step may be composed only of the water-soluble ethylenically unsaturated monomer or may contain an internal-crosslinking agent. Examples of the internal-crosslinking agent used herein include polyvalent glycidyl compounds such as ethylene diglycidyl ether, polyethylene diglycidyl ether, glycerol polyglycidyl ether, diglycerol polyglycidyl ether, ethylene glycol diglycidyl ether, polyethylene glycol diglycidyl ether, propylene glycol dialycidyl ether, polypropylene glycol diglycidyl ether, glycerol diglycidyl ether, and polyglycerol diglycidyl ether. Among these, ethylene glycol diglycidyl ether, polyethylene glycol diglycidyl ether, propylene glycol diglycidyl ether, polypropylene glycol diglycidyl ether, glycerol diglycidyl ether or polyglycerol diglycidyl ether is preferably used since a water-absorbent resin having a smaller amount of water-soluble substance, which shows high water-absorption capacity under load and excellent water-absorption rate, is likely to be obtained. The internal-crosslinking agent can be used in combination of two or more kinds.

The usage of the internal-crosslinking agent is not unconditionally determined since it differs depending on the type, but is usually preferably set to 0.000001 to 0.001 mol and more preferably set to 0.00001 to 0.01 mol, relative to 1 mol of the water-soluble ethylenically unsaturated monomer, from the viewpoint of reducing the water-soluble substance by achieving moderate crosslinking while maintaining sufficient water-absorption capacity in the intended water-absorbent resin.

The internal-crosslinking agent may be added to the aqueous solution of the water-soluble ethylenically unsaturated monomer, or may be added to the reaction system separately from the water-soluble ethylenically unsaturated monomer.

In the polymerization of the polymerizable component containing a water-soluble ethylenically unsaturated monomer, a water-soluble azo-type radical polymerization initiator is used. Examples of the usable water-soluble azo-type radical polymerization initiator include 1-[(1-cyano-1-methylethyl)azo]formamide, 2,2'-azobis[2-(N-phenylamidino)propane]dihydrochloride, 2,2'-azobis[2-[N-(4-chlorophenyl)amidino]propane]dihydrochloride, 2,2'-azobis[2-[N-(4-hydroxyphenyl)amidino]propane]dihydrochloride, 2,2'-azobis-[2-(N-benzylamidino)propane]dihydrochloride, 2,2'-azobis[2-(N-allylamidino)propane]dihydrochloride, 2,2'-azobis(2-amidinopropane)dihydrochloride, 2,2'-azobis[2-[N-(2-hydroxyethyl)amidino]propane]dihydrochloride, 2,2'-azobis[2-(5-methyl-2-imidazolin-2-yl)propane]dihydrochloride, 2,2'-azobis[2-(2-imidazolin-2-yl)propane]dihydrochloride, 2,2'-azobis[2-(4,5,6,7-tetrahydro-1H-1,3-diazepin-2-yl)dihydrochloride, 2,2'-azobis[2-(5-hydroxy-3,4,5,6-tetrahydropyrimidin-2-yl)propane]dihydrochloride, 2,2'-azobis[2-[1-(2-hydroxyethyl)-2-imidazolin-2-yl]propane]dihydrochloride, 2,2'-azobis[2-(2-imidazolin-2-yl)propane], 2,2'-azobis[2-methyl-N-[1,1-bis(hydroxymethyl)-2-hydroxyeth yl]propionamide], 2,2'-azobis[2-methyl-N-[1,1-bis(hydroxymethyl)ethyl]propionamide], 2,2'-azobis[2-methyl-N-(2-hydroxyethyl)-propionamide], 2,2'-azobis(2-methylpropionamide)dihydrate, 4,4'-azobis-4-cyanovaleric acid, 2,2'-azobis[2-(hydroxymethyl)propionitrile], 2,2'-azobis[2-(2-imidazolin-2-yl)propane]disulfate, 2,2'-azobis[N-(2-carboxyethyl)-2-methylpropionamidine]tetrahydrate, 2,2'-azobis[2-methyl-N-(2-hydroxyethyl)propionamide], and the like. Among these, 2,2'-azobis(2-amidinopropane) dihydrochloride, 2,2'-azobis[2-[1-(2-hydroxyethyl)-2-imidazolin-2-yl]propane]dihydrochloride or 2,2'-azobis[N-(2-carboxyethyl)-2-methylpropionamidine]tetrahydrate is particularly preferably used since a water-absorbent resin having a smaller amount of water-soluble substance and showing high water-retention capacity is obtained.

The water-soluble azo-type radical polymerization initiator can be used in combination of two or more kinds.

The polymerization method of the polymerizable component containing a water-soluble ethylenically unsaturated monomer is not particularly limited so long as it is a method capable of polymerizing a water-soluble ethylenically unsaturated monomer as an aqueous solution, and can be selected from the classic polymerization methods such as an aqueous polymerization method, an emulsion polymerization method, and a reversed-phase suspension polymerization method.

In the case of the aqueous polymerization method, a reaction vessel is charged with an aqueous solution of water-soluble ethylenically unsaturated monomer, water-soluble azo-type radical polymerization initiator, and optionally an internal-crosslinking agent, and polymerization can be progressed by heating while stirring as required. In the case of the reversed-phase suspension polymerization method, at least one of those among a surfactant and a polymeric protective colloid, an aqueous solution of a water-soluble ethylenically unsaturated monomer, a water-soluble azo-type radical polymerization initiator, and optionally an internal-crosslinking agent are charged to a hydrocarbon solvent, and polymerization can be progressed by heating while stirring.

The polymerization method preferred in the polymerization step is the reversed-phase suspension polymerization method since precise control of polymerization reaction is possible, and the particle size of the resulting water-absorbent resin can be controlled in a wide range. Hereinafter, the case of carrying out the polymerization step by a reversed-phase suspension polymerization method is described in more detail.

The hydrocarbon solvent used in the reversed-phase suspension polymerization method is not particularly limited, and examples thereof include aliphatic hydrocarbon solvents such as n-hexane n-heptane and ligroin; alicyclic hydrocarbon solvents such as cyclopentane, methylcyclopentane, cyclohexane and methylcyclohexane; aromatic hydrocarbons such as benzene, toluene and xylene; and the like. Among these, n-hexane, n-heptane or cyclohexane is preferably used since they are easily available industrially and inexpensive, and the quality is stable. The hydrocarbon solvent can be used in combination of two or more kinds.

The usage of the hydrocarbon solvent is usually preferably set to 50 to 600 parts by mass and more preferably set to 80 to 550 parts by mass, relative to 100 parts by mass of the water-soluble ethylenically unsaturated monomer, since it is easy to control the polymerization temperature by removal of the heat of polymerization.

Examples of the surfactant usable in the reversed-phase suspension polymerization method include nonionic surfactants such as sorbitan fatty acid esters, polyglyceryl fatty acid esters, sucrose fatty acid esters, sorbitol fatty acid esters and polyoxyethylene alkyl phenyl ethers; and anionic surfactants such as fatty acid salts, alkylbenzene sulfonates, alkyl methyl taurates, polyoxyethylene alkylphenyl ether sulfates and polyoxyethylene alkyl ether sulfonates; and the like. Among these, a nonionic surfactant, particularly, a sorbitan fatty acid ester, a polyglyceryl fatty acid ester or a sucrose fatty acid ester is preferably used.

Examples of the polymeric protective colloid include ethyl cellulose, ethylhydroxyethyl cellulose, polyethylene oxide, maleic anhydride-modified polyethylene, maleic anhydride-modified polybutadiene, a maleic anhydride-modified EPDM (ethylene/propylene/diene/terpolymer), and the like.

In the reversed-phase suspension polymerization method, one of those among the surfactant and the polymeric protective colloid may be used, or both can be used in combination. The usage of the surfactant and the polymeric protective colloid is preferably set to 0.1 to 5 parts by mass and more preferably 0.2 to 3 parts by mass, relative to 1.00 parts by mass of the water-soluble ethylenically unsaturated monomer, from the viewpoint of stability of a reversed-phase suspension polymerization system.

The usage of the water-soluble azo-type radical polymerization initiator is preferably set to 0.00005 to 0.001 mol and more preferably set to 0.0001 to 0.0008 mol, relative to 1 mol of the water-soluble ethylenically unsaturated monomer, since the polymerization reaction time can be shortened while preventing sudden polymerization reaction.

The reaction temperature at the time of polymerization reaction is usually preferably set to 20 to 110° C. and more preferably set to 40 to 90° C. since the reaction can be smoothly performed while easily removing the heat of polymerization, and economical efficiency can be improved owing to shorter polymerization time realized by rapid polymerization reaction. In this case, the polymerization reaction time can be usually from 0.5 to 4 hours.

The polymerization by the reversed-phase suspension polymerization method can be carried out in multiple stages by further adding the polymerizable component stepwise at once or in several times to a slurry obtained by progress of the polymerization of the polymerizable component. When the temperature of the slurry is high at the time of stepwise addition of the polymerizable component, it is preferred that the slurry is once cooled to room temperature, and then the polymerizable component is added. In addition, the number of times (the number of stages) of the polymerization in multi-stage polymerization is preferably set to two stages (the number of times of further addition of the polymerizable component is once) or three stages (the number of times of further addition of the polymerizable component is twice) that can reasonably enhance the productivity of the water-absorbent resin.

Next, the reaction system in which the polymerization reaction has completed, specifically, the reaction system containing a water-absorbent resin precursor, is heated, thereby removing water from the reaction system (dehydration step). Examples of the specific method for removing water from the reaction system include (a) a method of externally heating the reaction system in which a water-absorbent resin precursor is dispersed in a hydrocarbon solvent, and removing water by azeotropic distillation, (b) a method of separating a water-absorbent resin precursor from the reaction system by decantation and drying the reaction system containing the separated water water-absorbent resin precursor under reduced pressure while heating to remove water, (c) a method of separating a water-absorbent resin precursor using a filter and drying the reaction system containing the separated water-absorbent resin precursor under reduced pressure while heating to remove water, and the like. Among these methods, the method of (a) is suitably used as the operation is easy the reaction system contains an organic solvent such as a hydrocarbon solvent.

In the dehydration step, to the reaction system, water-soluble radical polymerization initiator is newly added, end a reducing substance is also added. The water-soluble radical polymerization initiator and the reducing substance are both preferably added to the reaction system as an aqueous solution. Each occasion of the addition of the water-soluble radical polymerization initiator and the reducing substance is decided according to the residual water rate of the reaction system. Specifically, the water-soluble radical polymerization initiator is added to the reaction system at any dehydration stage (first dehydration stage) when the residual water rate of the reaction system is 50% or more, preferably 55% or more, and more preferably 60% or more. On the other hand, the reducing substance is added to the reaction system at any dehydration stage (second dehydration stage) when the residual water rate decreases from that at the first dehydration stage by 10% or more, preferably by 15% or more, and more preferably by 20% or more. However, the second dehydration stage is preferably set in the stage in which water remains in the reaction system.

Herein, the residual water rate of the reaction system refers to the percentage of the mass of water remaining in the reaction system based on the mass of the water-soluble ethylenically unsaturated monomer used in the polymerization step, and is calculated by the following formula (1). In the formula (1), "Mass of Water Remaining in. Reaction System" means the total mass of water present in the reaction system at the calculation of the residual water rate, and is calculated by subtracting the mass of water removed from the reaction system at the calculation of the residual water rate from the amount of the material used in the polymerization step, and if applicable, the addition amount of the aqueous solutions such as the aqueous solution of the water-soluble radical polymerization initiator and the aqueous solution of the reducing substance added to the reaction system in the dehydration step.

[Formula 2]

$$\text{Residual Water Rate (\%)} = \frac{\text{Mass of Water Remaining in Reaction System}}{\text{Mass of Water-Soluble Ethylenically Unsaturated Monomer Used in Polymerization Step}} \times 100 \quad (1)$$

In the dehydration step, when the water-soluble radical polymerization initiator and the reducing substance are added in this order at the above-described stages, a part of the residual monomers that are present together with the water-absorbent resin precursor produced in the reaction system is polymerized by the water-soluble radical polymerization initiator, and also, a part of the residual monomers converted into another compound (derivative of the residual monomers) by the reaction with the reducing substance. Consequently, a water-absorbent resin in which the amount of residual monomers is significantly reduced is obtainable. The polymer of the residual monomers and the derivative of the residual monomers generated herein are stable substances, and an effect to the living body such as a human body, particularly, an effect to the skin, is less as compared to the residual monomers.

When the addition order of the water-soluble radical polymerization initiator and the reducing substance is inversed, specifically, when the reducing agent is added and then the water-soluble radical polymerization initiator is added to the reaction system, among the reducing substance added earlier, the residue that has failed to be involved in the reaction with the residual monomers tends to promote cleavage of the water-soluble radical polymerization initiator to be added later (radical generation). Therefore, the polymerization of the residual monomers in the reaction system is less likely to progress, and consequently the content of the residual monomers in the resulting water-absorbent resin is less likely to decrease.

In addition, when the er-soluble radical polymerization initiator is added after the residual water rate of the reaction system falls below 50%, the polymerization of the residual monomers is less likely to progress, then it becomes difficult to sufficiently reduce the content of the residual monomers the intended water-absorbent resin. Furthermore, when the reducing substance is added after the residual water rate falls to only less than 10% as compared to the first dehydration stage, the cleavage reaction (radical generation) of the water-soluble radical polymerization initiator added in advance tends to be extremely promoted, and consequently, the polymerization of the residual monomers is less likely to progress. As a result, it becomes difficult to sufficiently reduce the content of the residual monomers in the intended water-absorbent resin.

When the water-soluble radical polymerization initiator or the reducing substance is added to the reaction system, it is necessary to rapidly and smoothly progress the reaction of each additive with the residual monomers, and therefore, heating is required. In this regard, the heating temperature the reaction system in the dehydration step is usually preferably set to 40 to 110° C. and more preferably set to 50 to 90° C. In addition, the reaction time necessary after the addition of each additive is usually from 10 minutes to 3 hours or so. When the reaction system reaches the second dehydration stage within the necessary reaction time after the addition of the water-soluble radical polymerization initiator, the reducing substance may be added even within the reaction time.

Examples of the water-soluble radical polymerization initiator added to the reaction system in the dehydration step include persulfates such as potassium persulfate, ammonium persulfate and sodium persulfate; peroxides such as methyl ethyl ketone peroxide, methyl isobutyl ketone peroxide, di-t-butyl peroxide, t-butyl cumyl peroxide, t-butylperoxy acetate, t-butylperoxy isobutylate, t-butylperoxy pivalate and hydrogen peroxide; azo compounds such as 2,2'-azobis[2-(N-phenylamidino)propane]dihydrochloride, 2,2'-azobis[2-(N-allylamidino)propane]dihydrochloride, 2,2'-azobis[2-[1-(2-hydroxyethyl)-2-imidazolin-2-yl]propane]dihydrochloride, 2,2'-azobis{2-methyl-N-[1,1-bis(hydroxymethyl)-2-hydroxyethyl]propionamide}, 2,2'-azobis[2-methyl-N-(2-hydroxyethyl)-propionamide] and 4,4'-azobis(4-cyanovaleric acid); and the like. Among these, potassium persulfate, sodium persulfate or 2,2'-azobis[2-(N-phenylamidino)propane]dihydrochloride is preferably used since they are easily available industrially and have stable quality and high safety.

The water-soluble radical polymerization initiator may be used in combination of two or more kinds.

The amount of the water-soluble radical polymerization initiator added to the reaction system is preferably net to 0.01 to 0.15 mol % of the total amount of the water-soluble ethylenically unsaturated monomer used in the polymerization step. When the addition amount is less than 0.01 mol %, sufficient result in reducing residual monomers is possibly less likely to be obtained. In contrast, when the addition amount exceeds 0.15 mol %, water-absorption properties of the water-absorbent resin to be obtained may be impaired.

In addition, examples of the reducing substance added to the reaction system can include sulfurous acid and a salt thereof, hydrogen sulfite and a salt thereof, phosphorous acid and a salt thereof, hypophosphorous acid and a salt thereof, thiosulfuric acid and a salt thereof, and the like. Among these, sulfurous acid or a salt thereof, or hydrogen sulfite or a salt thereof is preferable since they are easily available industrially and have high safety, and their handling is easy.

The reducing substance may be used in combination of two or more kinds.

The amount of the reducing substance added to the reaction system is preferably set to 0.0001 to 0.002 mol % of the total amount of the water-soluble ethylenically unsaturated monomer used in the polymerization step. When the addition amount is less than 0.0001 mol %, a sufficient result in reducing residual monomers is possibly less likely to be obtained. In contrast, when the addition amount exceeds 0.002 mol %, water-absorption properties of the water-absorbent resin to be obtained may be impaired.

In the production method of the present invention, the water-absorbent resin precursor obtained in the polymerization step can be subjected to a post-crosslinking treatment. Since the water-absorbent resin obtainable by thereafter subjecting the precursor to a post-crosslink ng treatment has increased crosslinking density of a surface, the amount of water-soluble substance is decreased, and water-absorption capacity under load is increased.

The post-crosslinking treatment can be usually carried out in a suitable stage in the dehydration step. However, it is usually preferable to carry out the post-crosslinking treatment after a reducing substance is added in the dehydration step and the reaction thereof is progressed.

In the post-crosslinking treatment, a post-crosslinking agent is reacted with the water-absorbent resin precursor. The usable post-crosslinking agent is a polyfunctional post-crosslinking agent that can be reacted with a carboxyl group of the water-absorbent resin precursor, and examples thereof include compounds having two or more reactive functional groups such as dials, trials or polyols such as ethylene glycol, polyethylene glycol, propylene glycol, polypropylene glycol, 1,4-butanediol, trimethylolpropane, polyoxyethylene glycol, polyoxypropylene glycol, glycerin and polyglycerin; diglycidyl ether compounds such as ethylene glycol diglycidyl ether, polyethylene glycol diglycidyl ether, propylene glycol diglycidyl ether, polypropylene glycol diglycidyl ether, glycerol diglycidyl ether and polyglycerol diglycidyl ether; epihalohydrin compounds such as epichlorohydrin, epibromohydrin and α-methylepichlorohydrin; and isocyanate compounds such as 2,4-tolylene diisocyanate and hexamethylene diisocyanate.

Among these, a diglycidyl ether compound is preferable since a water-absorbent resin showing high water-absorption capacity under load and excellent water absorption rate and having a smaller amount of water-soluble substance is likely to be obtained. Particularly, ethylene glycol diglycidyl ether, propylene glycol diglycidyl ether, glycerol diglycidyl ether or polyethylene glycol diglycidyl ether is preferable since water solubility is high and handling properties as a crosslinking agent is fine. Among these, ethylene glycol diglycidyl ether and propylene glycol diglycidyl ether are more preferable since they can enhance swelling performance of the resulting water-absorbent resin particles.

The post-crosslinking agent can be used in combination of two or mote kinds.

The usage of the post-crosslinking agent can be variant depending on the type of the post-crosslinking agent, but is usually preferably set to 0.00001 to 0.01 mol, more preferably set to 0.00005 to 0.005 mol, and particularly preferably set to 0.0001 to 0.002 mol, relative to 1 mol of the water-soluble ethylenically unsaturated monomer used in the polymerization step. When the usage is less than 0.00001 mol, the crosslinking density of the water-absorbent resin is less likely to increase, thus it becomes difficult to reduce the water-soluble substance in the water-absorbent resin and to increase water-absorption capacity under load of the water-absorbent resin. In contrast, when the usage of the post-crosslinking agent exceeds 0.01 mol, the crosslinking reaction markedly progresses, thus water-retention capacity of the water-absorbent resin may decrease.

The reaction of the water-absorbent resin precursor with the post-crosslinking agent is preferably carried out in the presence or ater. For this reason, it is preferred that water remains in the reaction system when a post-crosslinking agent is added, and that a post-crosslinking agent is added to the reaction system as an aqueous solution. The amount of water (when the post-crosslinking agent is added as an aqueous solution, this amount includes the amount of water derived from the aqueous solution) in the reaction system at the time when the post-crosslinking agent is added to the reaction system can be adjusted depending on the factors such as the type of the water-absorbent resin precursor, particle size, and water content, but is usually preferably set to 5 to 300 parts by mass, more preferably set to 10 to 100 parts by mass, and particularly preferably set to 10 to 50 parts by mass, relative to 100 parts by mass of the water-soluble ethylenically unsaturated monomer used in the polymerization step. When the amount of water is less than 5 parts by mass, the crosslinking reaction is less likely to progress in the water-absorbent resin precursor, and thus it becomes difficult to increase water-absorption capacity under load of the water-absorbent resin. In contrast, when the amount of water exceeds 300 parts by mass, the crosslinking reaction is excessively promoted, and thus water-retention capacity of the water-absorbent resin may greatly decrease. The amount of water in the reaction system means the total amount of water remaining in the reaction system during dehydration and water supplied the reaction system as necessary for post-crosslinking.

The objective water-absorbent resin can be obtained, after completion of the reaction by a reducing substance in the dehydration step or after completion of post-crosslinking treatment, by removing a solvent such as hydrocarbon solvent and water remaining in the system. For example, when a reversed-phase suspension polymerization method is applied in the polymerization step, a powdery water-absorbent resin is obtained by removing the hydrocarbon solvent and water from the system. When an aqueous polymerization method is applied, usually, an aggregated water-absorbent resin is obtained, and it is preferred that this water-absorbent resin is appropriately pulverized into a powder.

Since a water-soluble radical polymerization initiator and a reducing substance are added in a specific order at a particular stage in the dehydration step, the polymerization or derivatization of the residual monomers is well progressed. Therefore, the content of the residual monomers in the water-absorbent resin obtainable by the production method of the present invention can usually be a trace amount of 100 ppm less, 90 ppm or less, or 80 ppm or less.

The water-absorbent resin obtainable by the production method of the present invention can be used in various fields of hygienic materials such as disposable diapers and sanitary articles, commodities such as pet sheets, agricultural materials such as water-retaining materials and soil conditioners, and industrial materials such as water blocking materials for electrical power cable and communication cable and dew-catchers. Since the content of residual monomers is a trace amount, the water-absorbent resin is safe for the human body, particularly for the skin, and thus is particularly suitably used in a hygienic material.

When the powdery water-absorbent resin obtainable by the production method of the present invention is intended to use in a hygienic material, the mass average particle size is preferably adjusted to 200 to 600 µm, more preferably adjusted to 250 to 500 µm, and particularly preferably adjusted to 300 to 400 µm. In the case of the reversed-phase suspension polymerization method, the mass average particle size can be adjusted to a preferred range by the control of polymerization conditions, the conditioning of pulverization, classification, and the like.

The water-absorbent resin obtainable by the production method of the present invention has a high absorption rate of saline solution, which can be within 60 seconds, or within 55 seconds or within 50 seconds, by setting the mass average particle size within the above range. Therefore, when the water-absorbent resin is used in a hygienic material, the amount of re-wet can be suppressed owing to the high diffusibility of urine and blood. When the mass average particle size of the water-absorbent resin is less than 200 µm, the presence of small particles becomes greater, and thus handling properties of the water-absorbent resin may be deteriorated due to dusting and the like. Also, when used as a hygienic material, gel blocking is likely to be caused at the time of water absorption, resulting in the possibility of lower diffusibility of water or increase the amount of re-wet. In contrast, when the mass average particle size exceeds 600 µm, the water-absorption rate decreases. Therefore, when used in a hygienic material, urine and blood cannot be rapidly absorbed, and thus their leakage from the material may happen.

The absorption rate of saline solution described above is a value measured according to the method described in Examples set forth below.

The water-absorbent resin having the mass average particle size adjusted to the above range is likely to achieve the water-absorption properties required in a hygienic material. Specifically, this water-absorbent resin shows a retention capacity of saline solution of 40 to 60 g/g and an absorption capacity of saline solution under a load of 4.14 kPa of 20 ml/g or more. The larger the numerical value of the absorption capacity of saline solution under a load of 4.14 kPa, the smaller the amount of re-wet of urine or blood even when a pressure is applied to a hygienic material. The retention capacity of saline solution and the absorption capacity of saline solution under a load of 4.14 kPa can be measured according to the corresponding method described in Examples set forth below.

The numerical values of the water-absorption rate of saline solution, the water-retention capacity of saline solution and the absorption capacity of saline solution under a load of 4.14 kPa described above are the properties generally achieved when the mass average particle size of the water-absorbent resin obtained by the well-known production method of polymerizing a polymerizable component containing a water-soluble ethylenically unsaturated monomer dissolved in water using a water-soluble azo-type radical polymerization initiator and removing water from the reaction system by heating, is adjusted to the range as described above, particularly when the precursor is subjected to the above-described post-crosslinking treatment. Therefore, according to the production method of the present invention, the content of the residual monomers in a water-absorbent resin obtained by well-known production method can be reduced without impairing the water-absorption capacity (water-absorbing properties).

In the production method of the present invention, when the water-absorbent resin precursor is subjected to a post-crosslinking treatment, the obtained water-absorbent resin has increased crosslinking density of a surface, and thus the water-soluble substance is decreased. Therefore, when used in a hygienic material, "skin irritation" and "sliminess" due to effusion of a water-soluble substance can be suppressed. When the amount of the post-crosslinking agent used at the time of post-crosslinking treatment is set to the range as described above, the volume of a water-soluble substance in the water-absorbent resin can be usually 20% by mass or less or 15% by mass or less in accordance with the amount of the post-crosslinking agent. The volume of a water-soluble substance is the value measured by the method described in Examples set forth below.

As the hygienic material using the water-absorbent resin obtained by the production method of the present invention, one formed by interposing an absorbent material containing the water-absorbent resin between a liquid-permeable sheet and a liquid-impermeable sheet is preferable.

The liquid-permeable sheet used herein may be, for example, a nonwoven fabric or a porous sheet, made of polyethylene resin, polypropylene resin, polyester resin or polyamide resin. The liquid-impermeable sheet may be, for example, a film made of a synthetic resin or a composite material composed of a synthetic resin and a nonwoven fabric. Examples of the synthetic resin usable for the film include polyethylene resin, polypropylene resin and polyvinyl chloride resin.

The absorbent material used herein may be substantially made from a water-absorbent resin, but is usually preferably a complex with a hydrophilic fiber. Examples of this complex preferably include those having a mixing structure in which a water-absorbent resin and a hydrophilic fiber are uniformly blended, a sandwich structure in which a water-absorbent resin is retained between layered hydrophilic fibers, or a packaging structure in which a mixture of a water-absorbent resin and a hydrophilic fiber is wrapped with a packaging sheet having liquid permeability, such as tissue paper. Examples of the hydrophilic fiber used in the complex include cellulose fibers such as a cotton-like pulp obtained from wood, a mechanical pulp, a chemical pulp and a semi-chemical pulp; artificial cellulose fibers such as rayon and acetate; and the like. The hydrophilic fiber may contain synthetic fibers such as polyamide resin fiber, polyester resin, fiber and polyolefin resin fiber.

EXAMPLES

The present invention will be specifically described below by way of examples and comparative examples, but the present invention is not limited to these examples and the like.

Example 1

<Polymerization Step>

A 1000 mL five-necked cylindrical round-bottom flask, equipped with an agitator, a reflux condenser, a dropping funnel, a thermometer and a nitrogen gas inlet tube was charged with 340 g of n-heptane, and 0.83 g of a sucrose fatty acid ester having an HLB of 3.0 (manufactured by Mitsubishi Chemical Corporation under the trade name of "S-370") was added. After the sucrose fatty acid ester was dissolved by heating while being dispersed, the mixture was cooled to 55° C.

Separately from the above, a 500 mL Erlenmeyer flask was charged with 92 g (1.03 mol) of an 80.5% by mass aqueous solution of acrylic acid. Thereto was added dropwise 147.6 g (0.77 mol) of a 20.9% by mass aqueous solution of sodium hydroxide while externally cooling the flask, to neutralize 75 mol % of acrylic acid. Further, 0.0552 g (0.00020 mol) of 2,2'-azobis(2-amidinopropane)dihydrochloride as water-soluble azo-type radical polymerization initiator and 0.0102 g (0.000059 mol) of ethylene glycol diglycidyl ether as an internal-crosslinking agent were added, to prepare an aqueous monomer solution for the first-stage polymerization.

Also, in a separate 500 ml Erlenmeyer flask, 128.8 g (1.44 mol) of an 80.5% by mass aqueous solution of acrylic acid was charged, and thereto was added dropwise 160.56 g (1.08 mol) of a 26.9% by mass aqueous solution of sodium hydroxide while externally cooling the flask, to neutralize 75 mol % of acrylic acid. Further, 0.0772 g (0.00028 mol) of 2,2'-azobis (2-amidinopropane)dihydrochloride as a water-soluble azo-type radical polymerization initiator and 0.0116 g (0.000067 mol) of ethylene glycol diglycidyl ether as an internal-crosslinking agent were added, to prepare an aqueous monomer solution for the second-stage polymerization. This aqueous monomer solution for the second-stage polymerization was cooled using an ice-water bath.

The total amount of the aqueous monomer solution for the first-stage polymerization was added to the five-necked cylindrical round-bottom flask while stirring and then dispersed. The inside of the flask was sufficiently replaced with nitrogen and then heated and the bath temperature was kept at 70° C. to carry out polymerization reaction for 1 hour. After the resulting polymeric slurry liquid was cooled to room temperature, the total amount of the aqueous monomer solution for the second-stage polymerization was added to the polymerized slurry liquid. The inside of the flask was again sufficiently replaced with nitrogen and then heated, and the bath temperature was kept at 70° C. to carry out the second-stage polymerization reaction for 2 hours.

<Dehydration Step>

After the completion of the second-stage polymerization, the five-necked cylindrical round-bottom flask was heated with an oil bath of 120° C., and azeotropic distillation of water and n-heptane in the reaction system was performed, thereby removing 174.8 g of water off the system while refluxing n-heptane (it was the first dehydration stage, and the residual water rate was 62%). Herein, an aqueous solution obtained by dissolving 0.3092 g (0.0011 mol) of potassium persulfate in 15.0 g of water was added, and the reaction system was kept at 80° C. for 20 minutes. Furthermore, azeotropic distillation of water and n-heptane was performed, thereby removing 43.7 g of water off the system while refluxing n-heptane (it was the second dehydration stage, and the residual water rate was 49%). Herein, an aqueous solution obtained by dissolving 0.2208 g (0.00175 mol) of sodium sulfite in 10.0 g of water was added, and the reaction system was kept at 80° C. for 20 minutes. Subsequently, azeotropic distillation of water and n-heptane was performed, thereby removing 62.3 g of water off the system while refluxing n-heptane (the residual water rate was 25%). Thereafter, 4.415 g (0.0007 mol) of a 2% aqueous solution of ethylene glycol diglycidyl ether as a post-crosslinking agent was added, and the reaction system was kept at 80° C. for 2 hours. Furthermore, n-heptane and water were vaporized to have the reaction system dried, thereby obtaining 228.2 g of a water-absorbent resin in which spherical particles were agglomerated.

Example 2

The same procedures were carried out as in Example 1 except that the amount of potassium persulfate added in the first dehydration stage was changed from 0.3092 g to 0.2319 g (0.0009 mol), to obtain 228.5 g of a water-absorbent resin in which spherical particles were agglomerated.

Example 3

The same procedures were carried out as in Example 1 except that the amount of sodium sulfite added in the second dehydration stage was changed from 0.2208 g to 0.1105 g (0.00088 mol), to obtain 228.8 g of a water-absorbent resin in which spherical particles were agglomerated.

Example 4

The same procedures were carried out as in Example 1 except that 0.3092 g of potassium persulfate added in the first dehydration stage was changed to 0.2724 g (0.0011 mol) of sodium persulfate, to obtain 228.8 g of a water-absorbent resin in which spherical particles were agglomerated.

Example 5

The same procedures were carried out as in Example 1 except that 0.2208 g of sodium sulfite added in the second dehydration stage was changed to 0.1823 g (0.00175 mol) of sodium bisulfite, to obtain 227.8 g of a water-absorbent resin in which spherical particles were agglomerated.

Example 6

The same procedures were carried out as in Example 1 except that 0.0829 g (0.00020 mol) of 2,2'-azobis[N-(2-carboxyethyl)-2-methylpropionamidine]tetrahydrate was used in place of 0.0552 g (0.00020 mol) of 2,2'-azobis(2-amidinopropane)dihydrochloride as a water-soluble azo-type radical polymerization initiator in the aqueous monomer solution for the first-stage polymerization, and 0.1160 g (0.00028 mol) of 2,2'-azobis[N-(2-carboxyethyl)-2-methylpropionamidine] tetrahydrate was used in place of 0.0772 g (0.00028 mol) of 2,2'-azobis(2-amidinopropane)dihydrochloride as water-soluble azo-type radical polymerization initiator in the aqueous monomer solution for the second-stage polymerization, to obtain 228.4 g of a water-absorbent resin in which spherical particles were agglomerated.

Example 7

The same procedures were carried out as in Example 1 except that the dehydration amount in the first dehydration stage (the amount of water removed off before adding potassium persulfate) was changed from 174.8 g (the residual water rate was 62%) to 196.7 g (the residual water rate was 52%), and the amount of water removed off the system after adding sodium sulfite and being kept at 80° C. for 20 minutes was changed from 62.3 g (the residual water rate was 25%) to 40.4 g (the residual water rate was 25%), to obtain 228.0 g of a water-absorbent resin in which spherical particles were agglomerated. In this case, the residual water rate at the second dehydration stage was 39%.

Comparative Example 1

The polymerization step was carried out in the same manner as in Example 1. After the completion of the second-stage polymerization in the polymerization step, the five-necked cylindrical round-bottom flask was heated with an oil bath of 120° C., and azeotropic distillation of water and n-heptane in the reaction system was performed, thereby removing 225.8 g of water off the system while refluxing n-heptane (the residual water rate was 25%). Thereafter, 4.415 g (0.0007 mol) of a 2% aqueous solution of ethylene glycol diglycidyl ether was added, and the reaction system was kept at 80° C. for 2 hours. Furthermore, n-heptane was vaporized to have the reaction system dried, thereby obtaining 228.2 g of a water-absorbent resin in which spherical particles were agglomerated.

Comparative Example 2

The polymerization step was carried out in the same manner as in Example 1. After the completion of the second-stage polymerization in the polymerization step, the five-necked cylindrical round-bottom flask was heated with an oil bath of 120° C., and azeotropic distillation of water and n-heptane in the reaction system was performed, thereby removing 218.5 g of water off the system while refluxing n-heptane (the residual water rate was 42%). Herein, an aqueous solution obtained by dissolving 0.2208 g (0.00175 mol) of sodium sulfite in 10.0 g of water was added, and the reaction system was kept at 80° C. for 20 minutes. Subsequently, azeotropic distillation of water and n-heptane was performed, thereby removing 47.3 g of water off the system while refluxing n-heptane (the residual water rate was 25%). Thereafter, 4.415 g (0.0007 mol) of a aqueous solution of ethylene glycol diglycidyl ether was added, and the reaction system was kept at 80° C. for 2 hours. Furthermore, n-heptane and water were vaporized to have the reaction system dried, thereby obtaining 227.8 g of water-absorbent resin in which spherical particles were agglomerated.

Comparative Example 3

The same procedures were carried out as in Comparative Example 2 except that the amount of sodium sulfite was changed from 0.2208 g to 0.6624 g (0.00525 mol), to obtain 226.8 g of a water-absorbent resin in which spherical particles were agglomerated.

Comparative Example 4

The polymerization step was carried out in the same manner as in Example 1. After the completion of the second-stage polymerization in the polymerization step, the five-necked cylindrical round-bottom flask was heated with an oil bath of 120° C., and azeotropic distillation of water and n-heptane in the reaction system was performed, thereby removing 174.8 g of water off the system while refluxing n-heptane (the residual water rate was 62%). Herein, an aqueous solution obtained by dissolving 0.3092 g (0.0011 mol) of potassium persulfate in 15.0 g of water was added, and the reaction system was kept at 80° C. for 20 minutes. Subsequently, azeotropic distillation of water and n-heptane was performed, thereby removing 96.0 g of water off the system while refluxing n-heptane (the residual water rate was 25%). Thereafter, 4.415 g (0.0007 mol) of a 2% aqueous solution of ethylene glycol diglycidyl ether was added, and the reaction system was kept at 80° C. for 2 hours. Furthermore, n-heptane and water were vaporized to have the reaction system dried, thereby obtaining 228.3 g of a water-absorbent resin in which spherical particles were agglomerated.

Comparative Example 5

The same procedures were carried out as in Comparative Example 4 except that the amount of potassium persulfate was changed from 0.3092 g to 1.1043 g (0.0041 mol), to obtain 225.9 g of a water-absorbent resin in which spherical particles were agglomerated.

Comparative Example 6

The polymerization step was carried out in the same manner as in Example 1. After the completion of the second-stage polymerization in the polymerization step, an aqueous solution obtained by dissolving 1.1043 g (0.0041 mol) of potassium persulfate in 15.0 g of ter was added to the reaction system. Then, the flask heated with an oil bath of 120° C., and azeotropic distillation of water and n-heptane was performed, thereby removing 270.8 g of water off the system while refluxing n-heptane (the residual water rate was 25%). Herein, 4.415 g (0.0007 mol) of a 2% aqueous solution of ethylene glycol diglycidyl ether was added, and the reaction system was kept at 80° C. for 2 hours. Furthermore, n-heptane and water were vaporized to have the reaction system dried, thereby obtaining 228.6 g of a water-absorbent resin in which spherical particles were agglomerated.

Comparative Example 7

The polymerization step was carried out in the same manner as in Example 1. After the completion of the second-stage polymerization in the polymerization step, the five-necked cylindrical round-bottom flask was heated with an oil bath of 120° C., and azeotropic distillation of water and n-heptane in the reaction system was performed, thereby removing 174.8 g of water off the system while refluxing n-heptane (the residual water rate was 62%). Herein, an aqueous solution obtained by dissolving 0.3092 g (0.0011 mol) of potassium persulfate in 15.0 g of water and an aqueous solution obtained by dissolving 0.2208 g (0.00175 mol) of sodium sulfite in 10.0 g of water were added at the same time, and the reaction system was kept at 80° C. for 20 minutes. Then, azeotropic distillation of water and n-heptane was performed, thereby removing 106.0 g of water off the system while refluxing n-heptane (the residual water rate was 25%). Thereafter, 4.415 g (0.0007 mol) of a 2% aqueous solution of ethylene glycol diglycidyl ether was added, and the reaction system was kept at 80° C. for 2 hours. Furthermore, n-heptane and water were vaporized to have the reaction system dried, thereby obtaining 227.0 g of a water-absorbent resin in which spherical particles were agglomerated.

Comparative Example 8

The polymerization step was carried out in the same manner as in Example 1. After the completion of the second-stage polymerization in the polymerization step, the five-necked cylindrical round-bottom flask was heated with an oil bath of 120° C., and azeotropic distillation of water and n-heptane in the reaction system was performed, thereby removing 174.8 g of water off the system while refluxing n-heptane (it was the first dehydration stage, and the residual water rate was 62%). Herein, an aqueous solution obtained by dissolving 0.2208 g (0.00175 mol) of sodium sulfite in 10.0 g of water was added, and the reaction system was kept at 80° C. for 20 minutes. Furthermore, azeotropic distillation of water and n-heptane was performed, thereby removing 43.7 g of water off the system while refluxing n-heptane (it was the second dehydration stage, and the residual water rate was 42%). Herein, an aqueous solution obtained by dissolving 0.3092 g (0.0011 mol) of potassium persulfate in 15.0 g of water was added, and the reaction system was kept at 80° C. for 20 minutes. Subsequently, azeotropic distillation of water and n-heptane was performed, thereby removing 62.3 g of water off the system while refluxing n-heptane (the residual water rate was 25%). Thereafter, 4.415 g (0.0007 mol) of a 2% aqueous solution of ethylene glycol diglycidyl ether was added, and the reaction system was kept at 80° C. for 2 hours. Furthermore, n-heptane and water were vaporized to have the reaction system dried, thereby obtaining 228.3 g of a water-absorbent resin in which spherical particles were agglomerated.

Evaluation

With respect to the water-absorbent resins obtained in the respective examples and comparative examples, retention capacity of saline solution, water-absorption capacity under load, content of residual monomers, absorption rate of saline solution and water-soluble substance were measured by the following methods. The results are shown in Table 1.

(Retention Capacity of Saline Solution)

In a 500 mL beaker, 500 g of a 0.9% by mass aqueous salt solution (physiological saline) was charged, and then 2.0 g of the water-absorbent resin was dispersed while stirring at 600 r/min. so as not to generate an unswollen lump. The physiological saline was left under stirring for 30 minutes so that the water-absorbent resin was sufficiently swollen, then the whole content of the beaker was poured into a cotton bag (cotton-broad cloth No. 60, width 100 mm×length 200 mm). The cotton bag of which upper part was tied up with a rubber band was dehydrated for 1 minute with a dehydrator (manufactured by Kokusan Enshinki Co., Ltd. under the product number "H-122") set to have a centrifugal force of 167 G, then the mass Wa (g) of the cotton bag containing the swollen gel after the dehydration was measured. In addition, the same procedures were carried out without adding the water-absorbent resin to physiological saline, and the blank mass Wb (g) of the cotton bag upon wetting was measured. Then, the retention capacity of saline solution was calculated by the following formula.

[Formula 3]

Retention Capacity of Saline Solution (g/g) =

$$\frac{[Wa - Wb] \; (g)}{\text{Mass of Water-Absorbent Resin (g)}}$$

(Water-Absorption Capacity Under Load)

Using a measuring apparatus 100 schematically shown in FIG. 1, the measurement was made. In the drawing, the measuring apparatus 100 includes a burette section 1, a conduit 2, a measurement stage 3, and a measurement section 4 placed on the measurement stage 3. The burette section 1 includes a burette 10. In this burette 10, the upper portion is closable by a rubber stopper 14, and an air inlet tube 11 and a cock 12 are connected to the lower portion. The air inlet tube 11 has a cock 13 at the tip. The conduit 2 has an inner diameter of 6 mm, and connects the cock 12 of the burette section 1 with the measurement stage 3. The height of the measurement stage 3 is vertically adjustable. The measurement stage 3 is provided with a hole (conduit port) having a diameter of 2 mm at the center, to which one end of the conduit 2 is connected. The measurement section 4 includes a cylinder 40 made of plexiglass, a polyamide mesh 41 bonded to the bottom of the cylinder 40, and a weight 42 which is vertically movable in the cylinder 40. The cylinder 40 can be disposed on the measurement stage 3 and the inner diameter thereof is 20 mm. The sieve opening size of the polyamide mesh 41 is 75 μm (200 mesh). The weight 42 has a diameter of 19 mm and a mass of 119.6 g. As described below, the weight 42 is used for applying a load of 4.14 kPa to a water-absorbent resin 5 spread uniformly over the polyamide mesh 41.

The water-absorption capacity under load by this measuring apparatus 100 was measured in a room at 25° C. The specific procedure is as follows. First, the cocks 12 and 13 of the burette section 1 were closed and 0.9% by mass salt solution (physiological saline) adjusted to 25° C. was charged from the upper portion of the burette 10. Next, the upper portion of the burette 10 was closed by the rubber stopper 14, and the cocks 12 and 13 were opened. Then, the height of the measurement stage 3 was adjusted so that the water level of physiological saline coming out from the conduit port of the measurement stage 3 through the conduit 2 is even with the upper surface of the measurement stage 3. In the measurement section 4, 0.10 g of the water-absorbent resin 5 was uniformly spread over the polyamide mesh 41 in the cylinder 40, and the weight 42 was placed on the water-absorbent resin 5. Then, the cylinder 40 was disposed on the measurement stage 3 so that an axis line thereof agrees with the conduit port of the measurement stage 3.

A decrease in the amount of physiological saline (i.e., amount of physiological saline absorbed in the water-absorbent resin 5) Wc (ml) in the burette 10 was read 60 minutes after the beginning of absorption of physiological saline from the conduit 2 by the water-absorbent resin 5. The water-absorption capacity under load of the water-absorbent resin 5 was calculated by the following formula.

[Formula 4]

$$\text{Water-Absorption Capacity under Load (ml/g)} = \frac{Wc \text{ (ml)}}{\text{Mass of Water-Absorbent Resin (g)}}$$

(Content of Residual Monomers)

In a 500 mL beaker, 500 g of a 0.9° by mass aqueous salt solution (physiological saline) was charged, then 2.0 g of the water-absorbent resin was added, and the mixture was stirred for 60 minutes. The content in the beaker was passed through a JIS (Japan Industrial Standard) standard sieve with a sieve opening of 75 μm, then filtrated with a filter paper (No. 3 manufactured by ADVANTEC), to separate a water-absorbed gel and an extraction liquid (physiological saline). The amount of monomers dissolved in the obtained extraction liquid was measured by high-performance liquid chromatography. The monomers to be measured herein were acrylic acid and alkali metal salts thereof. The measured value was converted into the value per mass of the water-absorbent resin, and was defined as the content of residual monomers (ppm).

(Absorption Rate of Saline Solution)

The measurement was carried out in a room adjusted to 25° C.±1° C. A magnetic stirrer bar (8 mmϕ×30 mm with no ring) was put in a 100 mL beaker in which 50±0.1 g of physiological saline had been charged. Then, this beaker was immersed in a constant-temperature water bath to adjust the solution temperature to 25±0.2° C. Next, the beaker was placed on a magnetic stirrer (manufactured by Iuchi under the product number "HS-30D") to generate a vortex in physiological saline at a rotational speed of 600/min. Then, 2.0±0.002 g of the water-absorbent resin was quickly added to the beaker. The elapsed time (seconds) from the point of the completion of adding the water-absorbent resin to the point where a vortex on the liquid surface vanished was measured using a stopwatch, which was defined as an absorption rate of saline solution of water-absorbent resin particles.

(Water-Soluble Substance)

A magnetic stirrer bar (8 mmϕ×30 mm with no ring) was put in a 500 mL beaker in which 500±0.1 g of physiological saline had been charged. Then, this beaker was placed on a magnetic stirrer (manufactured by Iuchi under the product number "HS-30D"). The magnetic stirrer bar was adjusted so as to have a rotational speed of 600 r/min., and also adjusted so that the bottom of the vortex generated by the rotation thereof came close thereto.

Next, the water-absorbent resin was classified using two kinds of standard sieves complying with JIS-Z8801-1982 (one has the sieve opening of 500 μm, and the other has that of 300 μm), to adjust the particle size of the water-absorbent resin to 500 μm or less and 300 μm or more. Then, 2.0±0.002 g of the water-absorbent resin was dispersed in the solution in the beaker by quickly pouring it between the center of vortex generated in the beaker and the side-wall of the beaker, and was stirred for 3 hours. Then, the aqueous dispersion of the water-absorbent resin after stirring for 3 hours was filtered with a standard sieve (sieve opening: 75 μm) and the resulting filtrate was further subjected to suction filtration using a Kiriyama type funnel with the filter paper of No. 6. In a 100 mL beaker heat-processed beforehand to be a constant weight, 80±0.1 g of the resulting filtrate was poured. The filtrate was dried up with a hot air drier (product of ADVANTEC) at 140° C. until a constant weight was attained, and the mass Wd (g) of the solid content of the filtrate was measured. Also, the same procedures as the above were carried out without using the water-absorbent resin, and the mass We (g) of the solid content of the filtrate was measured. The volume of the water-soluble substance in the water-absorbent resin as calculated on the basis of the following formula.

[Formula 5]

$$\text{Water-Soluble Substance (\% by Mass)} = \frac{(Wd - We) \times \left(\frac{500}{80}\right)}{2} \times 100$$

TABLE 1

| | Retention Capacity of Saline Solution (g/g) | Water-Absorption Capacity Under Load (ml/g) | Content of Residual Monomers (ppm) | Absorption Rate of Saline Solution (Seconds) | Water-Soluble Substance (% by Mass) |
|---|---|---|---|---|---|
| Example 1 | 42 | 20 | 32 | 39 | 12 |
| Example 2 | 45 | 21 | 70 | 41 | 14 |
| Example 3 | 41 | 23 | 75 | 40 | 12 |
| Example 4 | 44 | 20 | 40 | 41 | 13 |
| Example 5 | 41 | 23 | 46 | 39 | 11 |

TABLE 1-continued

|  | Retention Capacity of Saline Solution (g/g) | Water-Absorption Capacity Under Load (ml/g) | Content of Residual Monomers (ppm) | Absorption Rate of Saline Solution (Seconds) | Water-Soluble Substance (% by Mass) |
|---|---|---|---|---|---|
| Example 6 | 42 | 24 | 50 | 40 | 12 |
| Example 7 | 40 | 20 | 60 | 40 | 11 |
| Comparative Example 1 | 42 | 24 | 1448 | 41 | 12 |
| Comparative Example 2 | 42 | 22 | 337 | 41 | 11 |
| Comparative Example 3 | 43 | 13 | 94 | 40 | 13 |
| Comparative Example 4 | 44 | 16 | 400 | 39 | 12 |
| Comparative Example 5 | 43 | 16 | 185 | 40 | 11 |
| Comparative Example 6 | 42 | 18 | 118 | 40 | 12 |
| Comparative Example 7 | 43 | 17 | 220 | 42 | 13 |
| Comparative Example 8 | 42 | 22 | 308 | 40 | 12 |

As is apparent from Table 1, the water-absorbent resins obtained in Examples 1 to 7 all demonstrate favorable water-absorption capacity and reduced content of residual monomers. By contrast, favorable water-absorption capacity does not coexist with reduced content of residual monomers with respect to the water-absorbent resins obtained in Comparative Examples 1 to 8.

The present invention can be carried out in other specific forms without departing from the spirit or essential properties thereof. The above embodiment and example are therefore to be considered in all respects as illustrative and not restrictive. The scope of the present invention is indicated by the appended claims rather than by the foregoing description. All changes and modifications which come within the range of equivalency of the claims are therefore intended to be included within the scope of the present invention.

The invention claimed is:

1. A method for producing a water-absorbent resin, comprising:
   a polymerization step of polymerizing a polymerizable component containing a water-soluble ethylenically unsaturated monomer dissolved in water using a water-soluble azo-type radical polymerization initiator to obtain a reaction system comprising a water-absorbent resin precursor, and
   a dehydration step of removing water from the reaction system by heating,
   wherein, in the dehydration step, a water-soluble radical polymerization initiator is added to the reaction system at any first dehydration stage when the residual water rate calculated by the following formula (1) is 50% or more, and a reducing substance is added to the reaction system at any second dehydration stage when the residual water rate decreases from that at the first dehydration stage by 10% or more, wherein the residual water rate (%) is determined by the following Formula (1):

$$\left[\frac{\text{mass of water remaining in the reaction system}}{\text{mass of the water-soluble ethylenically unsaturated monomer used in the polymerization step}}\right] \times 100. \quad \text{[Formula 1]}$$

2. The method for producing a water-absorbent resin according to claim 1, wherein the polymerizable component is polymerized by a reversed-phase suspension polymerization method in the polymerization step.

3. The method for producing a water-absorbent resin according to claim 2, wherein the polymerizable component is further added to be polymerized to a slurry obtained by progress of the polymerization of the polymerizable component.

4. The method for producing a water-absorbent resin according to claim 3, wherein the addition of the polymerizable component to the slurry and the polymerization are repeated.

5. The method for producing a water-absorbent resin according to claim 1, wherein the water-soluble azo-type radical polymerization initiator is at least one selected from the group consisting of 2,2'-azobis(2-amidinopropane)dihydrochloride, 2,2'-azobis[2-[1-(2-hydroxyethyl)-2-imidazolin-2-yl]propane]dihydrochloride, and 2,2'-azobis[N-(2-carboxyethyl)-2-methylpropionamidine]tetrahydrate.

6. The method for producing a water-absorbent resin according to claim 1, wherein the water-soluble radical polymerization initiator is at least one selected from the group consisting of potassium persulfate, sodium persulfate, and 2,2'-azobis[2-(N-phenylamidino)propane]dihydrochloride.

7. The method for producing a water-absorbent resin according to claim 1, wherein the reducing substance is at least one selected from the group consisting of sulfurous acid, a sulfite, hydrogen sulfite and a bisulfite.

8. The method for producing a water-absorbent resin according to claim 1, wherein the amount of the water-soluble radical polymerization initiator added to the reaction system is 0.01 to 0.15 mol % of the total amount of the water-soluble ethylenically unsaturated monomer used in the polymerization step.

9. The method for producing a water-absorbent resin according to claim 1, wherein the amount of the reducing substance added to the reaction system is 0.0001 to 0.002 mol % of the total amount of the water-soluble ethylenically unsaturated monomer used in the polymerization step.

10. The method for producing a water-absorbent resin according to claim 1, wherein the water-absorbent resin precursor is subjected to a post-crosslinking treatment in the dehydration step.

11. A water-absorbent resin obtainable by the method for producing a water-absorbent resin as defined in claim 1,
   wherein the content of residual monomers is 100 ppm or less, and
   which is in powdery form having a mass average particles size of 200 to 600 μm and has a retention capacity of saline solution of 40 to 60 g/g and an absorption capacity of saline solution under a load of 4.14 kPa of 20 ml/g or more.

12. A hygienic material comprising a liquid-permeable sheet, a liquid-impermeable sheet, and an absorbent material retained between these sheets,
   wherein the absorbent material comprises the water-absorbent resin as defined in claim 11.

13. The hygienic material according to claim 12, wherein the absorbent material is a composite of the water-absorbent resin and a hydrophilic fiber.

* * * * *